United States Patent [19]

Katagiri et al.

[11] Patent Number: 4,990,607
[45] Date of Patent: Feb. 5, 1991

[54] ALTERATION OF GENE EXPRESSION IN PLANTS

[75] Inventors: Fumiaki Katagiri; Eric Lam, both of New York; Nam-Hai Chua, Scarsdale, all of N.Y.

[73] Assignee: The Rockefeller University, New York, N.Y.

[21] Appl. No.: 323,533

[22] Filed: Mar. 14, 1989

[51] Int. Cl.$^5$ .................. C07H 21/04; C21N 5/00; C21N 15/00; C12P 21/02
[52] U.S. Cl. .................. 536/27; 435/69.1; 435/70.1; 435/172.3; 435/240.4; 435/317.1; 800/205; 935/35; 935/67
[58] Field of Search .............. 800/1; 435/240.4, 317.1, 435/172.3, 172.1; 935/35

[56] References Cited

PUBLICATIONS

Katagiri et al., 1989, (Aug.), Nature 340: 727-730.
Fromm et al., 1989 (Oct.) The Plant Cell 1:977-984.
Friedman et al., 1988, (Sep.) Nature, 335-452.
Sadowski et al., 1988 (Oct.) Nature 335:563.
Benfey et al., 1989 (Aug.) EMBO J. 8:2195-2202.
Willmitzer (Jan.) 1988, Trends in Genetics 4:13-18.
Green et al., 1987, EMBO J. 6:2543-2549.
Maier et al., 1987, EMBO J., 6:17-22.

Primary Examiner—Charles F. Warren
Assistant Examiner—P. Rhodes
Attorney, Agent, or Firm—Dennis R. Hoerner, Jr.; Thomas P. McBride; Howard C. Stanley

[57] ABSTRACT

A transacting DNA binding factor is disclosed. The ASF-1 protein factor specifically binds to the sequence motif TGACG found upstream of the promoter in many plant genes. Co-expression of this protein factor augments the level of expression of the up-regulated promoter containing the TGACG motif.

12 Claims, 3 Drawing Sheets

```
            GAATTCTTCAACGTACACCCAATTTGCTGCCTCAAGAAGGATGGGTATATGCGATCCG    58
              N  S  S  T  Y  T  Q  F  A  A  S  R  R  M* G  I  C  D  P    19

59    ATCCATCAACTTGGCATGTGGGATGATTTCAATAGTAGTTTCCCAAGTACATCGGCAACC    118
  20      I  H  Q  L  G  M  W  D  D  F  N  S  S  F  P  S  T  S  A  T     39

119    ATGATTTTAGAAGTTGATAAATGCCTAGAGGACCAGATACCAATTATGGAGAAAAGACTA    178
  40      M  I  L  E  V  D  K  C  L  E  D  Q  I  P  I  M  E  K  R  L     59

179    GACAACGAGACAGAAGACACTTCGCATGGAACAGTAGGGACTTCTAACAGATATGAACCG    238
  60      D  N  E  T  E  D  T  S  H  G  T  V  G  T  S  N  R  Y  E  P     79

239    GAAACAAGTAAACCCGTCGAGAAGGTACTTAGACGTCTTGCACAAAACCGCGAGGCTGCT    298
  80      E  T  S  K  P  V  E  K  V  L  R  R  L  A  Q  N  R  E  A  A     99

299    CGTAAAAGCCGTTTGCGGAAGAAGGCCTATGTTCAGCAGTTAGAAAATAGTAAATTGAAG    358
 100      R  K  S  R  L  R  K  K  A  Y  V  Q  Q  L  E  N  S  K  L  K    119

359    CTGATTCAACTGGAACAAGAACTAGAACGCGCCAGAAAACAGGGCATGTGTGTAGGTGGT    418
 120      L  I  Q  L  E  Q  E  L  E  R  A  R  K  Q  G  M  C  V  G  G    139

419    GGTGTAGATGCTAGCCAGCTAAGTTACTCTGGAACCGCTAGCTCAGGAACTGCTGTATTT    478
 140      G  V  D  A  S  Q  L  S  Y  S  G  T  A  S  S  G  T  A  V  F    159

479    GATATGGAGTATGGTCACTGGGTAGAAGAGCAAACTAGACAAACAAATGACTTAAGGATT    538
 160      D  M  E  Y  G  H  W  V  E  E  Q  T  R  Q  T  N  D  L  R  I    179

539    GCTTTGCATTCTCAAATTGGTGAAGCGGAATTGCGCATTATTGTTGATGGTTACCTGAAC    598
 180      A  L  H  S  Q  I  G  E  A  E  L  R  I  I  V  D  G  Y  L  N    199
```

\* putative translational
  start site

FIGURE 1(A)

```
599   CACTACTTTGATCTCTTCCGCATGAAAGCTACGGCTGCTAAAGCTGATGTCCTATACATC   658
200    H  Y  F  D  L  F  R  M  K  A  T  A  A  K  A  D  V  L  Y  I   219

659   ATGTCTGGTATGTGGAAGACATCTGCCGAGCGCTTTTTCATGTGGATTGGAGGGTTTCGG   718
220    M  S  G  M  W  K  T  S  A  E  R  F  F  M  W  I  G  G  F  R   239

719   CCATCCGAGCTTCTAAAGGTTCTCACACCGCATCTTGAGCTCTTGACAGAACAACAACTT   778
240    P  S  E  L  L  K  V  L  T  P  H  L  E  L  L  T  E  Q  Q  L   259

779   CGAGAGGTTTGTAACCTGACCCAATCATGTCAGCAAGCAGAAGACGCCTTGTCACAAGGA   838
260    R  E  V  C  N  L  T  Q  S  C  Q  Q  A  E  D  A  L  S  Q  G   279

839   ATGGTAAAACTCCACCAGATTCTTGCCGAGGCTGTTGCAGCTGGCCGACTAGGAGAAGGA   898
280    M  V  K  L  H  Q  I  L  A  E  A  V  A  A  G  R  L  G  E  G   299

899   AATTACACTCTTCCGCAGATGGGGCCTGCCATCGAAAAGTTGGAAGATCTTGTTAGGTTC   958
300    N  Y  T  L  P  Q  M  G  P  A  I  E  K  L  E  D  L  V  R  F   319

959   GTAAATCAGGCGGATCATCTACGACAAGAAACCCTCCAACAGATGTCCCGCATCCTTAAT   1018
320    V  N  Q  A  D  H  L  R  Q  E  T  L  Q  Q  M  S  R  I  L  N   339

1019  ACGTGCCAAGCAGCTCAGGGCTTACTTGCCTTAGGGGAGTACTTTGAACGACTTCGTGTT   1078
340    T  C  Q  A  A  Q  G  L  L  A  L  G  E  Y  F  E  R  L  R  V   359

1079  TTAAGCTCACAATGGGCTACTCGTCTACGTGAGCCTACCTAATGAAGCACAAGAAGATCC   1138
360    L  S  S  Q  W  A  T  R  L  R  E  P  T  *end of reading frame
```

FIGURE 1(B)

```
1139  GCTGTATATTACTCGAGGAGTTTTGCCTTCAGAAGATGATGCTGTGTTATGGACCAGAGT  1198

1199  ACTGTTGCTCACTTGGTATCTAAACCTATATAATCAGTGGCGGAGCCACACAGGTTCAAG  1258

1259  GGCAGATGCAAATTCAGGATTCCAATGTTATTCGAATCTATTATTTGTACTTATTTACTG  1318

1319  GATTTTAAACACATATATGTGATCTGAGCCAAAAACTACTAGGTTTGGATGAACCCATAA  1378

1379  GTTATACACTAGATCGGCTCCTGCTCAAGGGTGTTCAGTTGAGCATCCTTCGTCGGAAAA  1438

1439  TTATAGTGTGTTATATAAGTCAGATATTATGTGTTGAATCTTGAGCACACTTAGTGTAAT  1498

1499  TCTAGGCTTCGCCATTGAGCTATATTCATTCACTTCAGGTTTGTGGTGAATGAATTTTAC  1558

1559  CATCTTGCTACTTCTGGTAGGGTCTTGAGAACTTAAATGAGATTTTTACACAAATAGCC
```

FIGURE 1(C)

ALTERATION OF GENE EXPRESSION IN PLANTS

BACKGROUND OF THE INVENTION

The present invention relates to genetic engineering and more particularly to plant genetic engineering. In general, plant genetic engineering involves the introduction of a gene into the genome of a plant to cause expression of a protein in the plant cell or to control the expression of an endogenous plant protein. It is often desirable to be able to readily control the level of expression of a particular gene in plants Hence, the present invention provides a means to control expression of genes in plants by expressing a trans-acting DNA binding factor.

It is, therefore, the overall object of the present invention to provide a means to control gene expression in plants.

Accordingly, it is an object of the present invention to provide a means to augment the level of gene expression in all tissues or in specific tissues.

It is yet another object of the present invention to provide a trans-acting DNA binding factor to control expression of particular plant genes.

These and other objects and advantages of the present invention will be evident to those skilled in the art from the following description.

BRIEF DESCRIPTION OF GENE DRAWING

FIG. 1 represents the DNA sequence (and its deduced amino acid sequence) for clone hb1 which encodes a trans-acting DNA binding factor (ASF-1).

STATEMENT OF THE INVENTION

In one respect, the present invention provides a transacting DNA binding factor which is useful in the control of plant gene expression Specifically, a recombinant cDNA clone (hb1) encoding a trans-acting DNA binding factor which binds to the sequence TGACG has been isolated. The cDNA clone was identified by the ability of its gene product (protein) to bind specifically to a fragment of DNA containing the sequence GGTGACGTG which is found in the upstream region of the wheat histone H3 gene.

Cloning of the hb1 DNA Binding Factor

Various promoters of genes, not only in plant but also in animal, contain a TGACG motif in their upstream regions. Our study showed that the region which includes the direct repeat of TGACG motifs in CaMV35S promoter (as-1 sequence) has a very important role in the expression of 35S promoter in two ways: its expression in root and then conferring the effect of distal enhancers on the promoter. An as-1 sequence specific DNA binding factor (ASF-1) was characterized in vitro in pea and tobacco extracts. The in vitro study also showed that TGACG motifs in nopaline synthase gene promoter of Ti-plasmid (nos1 sequence) and histone H3 gene promoter of wheat (hex1 sequence) were recognized by similar binding factors.

For the further characterization of the DNA binding factors, the direct cloning of the genes for the factors was performed by means of screening an expression library with a radioactively labelled DNA binding site. An expression cDNA library was constructed in lambda gt11 vector with random-primed cDNA derived from polyA+ RNA of dark-adapted tobacco leaves. There were three reasons why the library was made from dark-adapted tobacco leaf RNA; because all of our in vivo study on cis-regulatory regions had been done in transgenic tobacco, genes for the factors are preferably isolated from the homologous system; the binding activity to as-1 sequence was observed to be much higher in the extract of dark-adapted tobacco leaves than in light-grown ones; the relative ratio of a certain mRNA species to total mRNA is higher in dark-adapted leaves because mRNA synthesis for photosynthetic machinery is shutdown. As the specific DNA sequence probe, a concatemerized hex1 sequence (CGCGGATTGGT GACGTGGCCG) was used because the structure of the TGACG containing region seemed more simple than those of the other binding sites. Five positive clones were obtained out of 60,000 recombinants after the primary screening. These clones were named lambda hb1, 2, 3, 5, and 6. Rescreening the filters with the wild-type probe (hex1) and a mutant probe (CGCGGATTTATGGCCG) in parallel demonstrated that only the wild-type probe bound to the proteins encoded by these recombinant phages. Lysogen extract made from lambda hb1 showed specific binding not only to hex1 sequence but also to as-1 sequence, nos1 sequence, and an upstream sequence of octopine synthase gene of Ti-plasmid, which has two TTACG motifs in it. A brief restriction mapping revealed that the sizes of the inserts in lambda hb1, 2, 5, and 6 are 1.2kb, 0.5kb, 1.2kb, 1.6kb, and 1.7kb, respectively.

FIG. 1 shows the nucleotide sequence (and deduced amino acid sequence) of the insert of clone hb1. The protein product (trans-acting DNA binding factor) bound specifically to a DNA fragment containing the sequence GGTGACGTG from the wheat histone H3 gene as well as DNA fragments found upstream of the cauliflower mosaic virus 35S gene and the nopaline synthase gene of the Ti plasmid of *Agrobacterium tumefaciens*.

Alteration of Gene Expression in Plants

While not fully understood, the data suggest that the transacting DNA binding factor (ASF-1) is able to bind to specific DNA sequences and is able to activate transcription from promoters that contain the specific DNA sequences. Factor ASF-1 recognizes the sequence motif TGACG which is found in plant genes such as histone genes (Mikami et al., 1987); enzyme genes for agropine biosynthesis (Velten et al., 1984); the octopine synthase gene (Ellis et al., 1987); and the mannopine synthase gene (DeRita and Gelvin, 1987); as well as the CaMV35S gene, histone H3 gene and nopaline synthase gene.

The recombinant cDNA clone encoding a trans-acting DNA binding factor able to bind specifically to sequences found upstream of the CaMV35S gene and upstream of cellular genes and able to activate transcription from these promoters can be used for many purposes. These purposes include but are not limited to the following:

1. Augmenting the levels of expression in all tissues or in specific tissues and under specific environmental conditions of cellular genes the promoters of which contain the binding site. This can be accomplished by causing expression of the ASF-1 protein encoded by the recombinant cDNA clone to be regulated by a promoter that confers expression in particular tissues or is responsive to particular environmental stimuli Examples of such promoters include but are not limited to the promoters from the genes for (i) the small subunit of ribulose bisphosphate carboxylase (rbcS) which is expressed primarily in tissue that contains chloroplasts and is responsive to light (Aoyagi et al., 1988), (ii) the chlorophyll A/B binding protein which is expressed in immature leaves, is responsive to light and is regulated by an internal circadian clock (Nagy et al., 1988), (iii) the heat-shock proteins, which are inducible by increases in ambient temperature (Strittmatter and Chua, 1987), (iv) the nopaline synthase promoter from *Agrobacterium tumefaciens* which is expressed in all tissues but is expressed preferentially in mature leaves and roots (An et al., 1986). The promoters from these genes would be placed upstream of the DNA fragment encoding the ASF-1 protein and the recombinant chimeric construct would be introduced into plants using standard techniques for generating transgenic plants.

2. Changing the levels of expression of cellular genes that contain the binding site by changing the structure of the protein encoded by the recombinant cDNA clone is another utility. It has been shown that trans-acting factors are frequently made up of at least two functional domains, one domain is responsible for binding DNA, the second domain is responsible for activating transcription (Ptashne, 1988). From comparison of the amino acid sequence of the ASF-1 protein with other trans-acting DNA binding proteins it appears likely that the ASF-1 protein contains these two types of domains. Modifications of the ASF-1 protein in order to change the levels of expression of cellular genes to which it binds can include but are not limited to the following:

(a) The activation domain can be replaced by an activation domain from another trans-acting factor. It has been shown that replacement of the activation domain of a yeast trans-acting factor, Gal-4, with the activation domain of a trans-acting factor from herpes simplex virus, VP16, results in a hybrid trans-acting factor with greatly increased activating potential (Sadowski et al., 1988). Replacement of the activating domain of ASF-1 with the activating domain of VP16 should result in increased activating potential of ASF-1. Replacement of the activating domain of ASF-1 with DNA fragments that encode putative activating domains, for example the highly acidic region of CaMV open reading frame IV (21 acidic residues and two basic residues out of 51 amino acid residues, Henle et al., 1982) could result in increased activating potential of ASF-1. In addition this would be a way of testing whether a putative activating domain could indeed function as an activating domain. Replacement of the activating domain of ASF-1 with the activating domain of the heat shock activating factor HSTF or HSF (Wiederrecht et al., 1988; Sorger and Pelham, 1988) could result in heat inducible expression of cellular genes that contain the binding site for ASF-1. Recombinant constructs containing the DNA encoding the chimeric proteins would be made and then fused to certain promoters including but not limited to the promoters listed above in section 1 and introduced into plants using standard techniques for generating transgenic plants.

(b) Expression of the DNA binding domain without an activation domain can result in inhibition of expression from genes which contain the binding site in the promoter (Friedman et al., 1988). Expression of the DNA binding domain of ASF-1 without an activation domain could result in inhibition of expression of genes that contain the binding site in the promoter. The cauliflower mosaic virus contains a binding site for ASF-1 upstream of the 35S gene promoter. The DNA fragment from the recombinant cDNA that encodes the DNA binding domain of ASF-1 would be fused to certain promoters including but not limited to the promoters listed in section 1 and introduced into plants using standard techniques for generating transgenic plants.

c) Expression of RNA that is complementary to the RNA that encodes a protein can result in inhibition of expression of the protein. The complementary RNA is termed "anti-sense RNA" (Green et al., 1986). Expression of anti-sense RNA complementary to the RNA encoding ASF-1 could result in a decreased concentration of the ASF-1 protein. If expression of a viral gene that contains the binding site for ASF-1 in its promoter is dependent upon a certain concentration of ASF-1 protein, expression of anti-sense RNA complementary to the ASF-1 RNA may cause inhibition of viral replication. The DNA fragment from the recombinant cDNA that encodes ASF-1 would be placed in an orientation so that RNA complementary to the RNA encoding ASF-1 would be produced and fused to certain promoters including but not limited to the promoters listed in section 1 and introduced into plants using standard techniques for generating transgenic plants.

Plant Gene Construction

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA. Transcription of DNA into mRNA is regulated by a region of DNA usually referred to as the "promoter." The promoter region contains a sequence of bases that signals RNA polymerase to associate with the DNA, and to initiate the transcription of mRNA using one of the DNA strands as a template to make a corresponding strand of RNA.

A number of promoters which are active in plant cells have been described in the literature. These include the nopaline synthase (NOS) and octopine synthase (OCS) promoters (which are carried on tumor-inducing plasmids of *Agrobacterium tumefaciens*). The cauliflower mosaic virus (CaMV) 19S and 35S promoters (Odell et al., 1985), the light-inducible promoter from the small subunit of ribulose bis-phosphate carboxylase (ssRUSICSO, a very abundant plant polypeptide), and the mannopine synthase promoter (Velten et al., 1984, and Velten & Schell, 1985). All of these promoters have been used to create various types of DNA constructs which have been expressed in plants, see e.g. PCT publication WO84/02913 (Rogers et al., Monsanto) Promoters which are known or are found to cause transcription of RNA in plant cells can be used in the present invention. Such promoters may be obtained from plants or viruses and include, but are not limited to, the CaMV35S promoter and promoters isolated from plant genes such as ssRUBISCO genes. As described below, it is preferred that the particular promoter selected should be capable of causing sufficient expression to result in the production of an effective amount of the ASF-1 protein to cause enhancement of the desired gene expression. The amount of ASF-1 protein needed may vary with the target promoter to be affected and the cell type or plant species. Accordingly, while the CaMV35S promoter is often preferred, it should be understood that this promoter may not be the optimal one for all embodiments of the present invention, particularly where selective expression of the ASF-1 protein is desired. The promoters used in the DNA constructs of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. Alternately, the strength of a promoter may be increased by inserting additional copies of enhancer elements as described by Kay et al., 1987. The resulting chimeric promoter may be used as described herein. For purposes of this description, the phrase "CaMV35S" promoter thus includes variations of CaMV35S promoter, e.g., promoters derived by means of ligation with different regulatory regions, random or controlled mutagenesis, addition of multiple enhancer elements, etc.

The DNA constructs of the present invention contain, in double-stranded DNA form, a structural gene sequence which encodes the ASF-1 protein. A coding sequence used in a DNA construct of this invention may be modified, if desired, to create mutants, either by random or controlled mutagenesis, using methods known to those skilled in the art. Such mutants and variants are therefore within the scope of the present invention Accordingly, the phrase "ASF-1 protein" is used here to include truncated proteins and fusion proteins, as well as unmodified ASF-1 protein.

The 3' non-translated region contains a polyadenylation signal which functions in plants to cause the addition of polyadenylate nucleotides to the 3' end of the mRNA. Examples of suitable 3' regions are (1) the 3' transcribed, non-translated regions containing the polyadenylated signal of genes from the T-DNA of *Agrobacterium*, the soybean storage protein genes and the small subunit of the RuBP carboxylase gene.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNAs, from suitable eukaryotic genes, or from a synthetic gene sequence. The non-translated leader sequence can be part of the promoter sequence, or can be derived from an unrelated promoter or coding sequence as discussed above.

Plant Transformation/Regeneration

A DNA construct of the present invention can be inserted into the genome of a plant by any suitable method. Suitable plant transformation vectors include those derived from a Ti plasmid of *Agrobacterium tumefaciens*, such as those described by Herrera-Estrella (1983), Bevan (1983), Klee (1985), Fraley (1985) and EPO publication 120,516 (Schilperoort, et al.). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, transformation using viruses or pollen and the use of microprojectiles.

Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, rapeseed, etc.), Cucurbitaceae (melons and cucumber), Gramineae (wheat, rice, corn, etc.), Solanaceae (potato, tobacco, tomato, peppers) and various floral crops. Gene expression can be altered in plants from each of the aforesaid families pursuant to the present invention.

BIBLIOGRAPHY

An, et al. (1986) *Mol. Gen. Genet.* 203:245.
Aoyagi, et al. (1988) *Mol. Gen. Genet.* 213:179.
Bevan, M. et al. (1983) *Nature* 304:184.
DiRita and Gelvin (1987) *Mol. Gen. Genet.* 207:233.
Ellis, et al. (1987) *EMBO J.* 6:3203.
Fraley, R. T. and Rogers, S. et al. (1985) *Biotechnology* 3:629.
Friedman et al. (1988) *Nature* 335:452.
Green, et al. (1986) *Ann. Rev. Biochem.* 55:569.
Henle, et al. (1982) *Current Topics in Microbiol. and Immunol.* 96:193.
Herrera-Estrella, L. et al. (1983) *Nature* 303:209.
Kay, R. et al. (1987) ScienceI 236:1299-1302.
Klee, H. J. et al. (1985) *Bio/Technology* 3:637-642
Kozak, M. (1984) *Nature* 308:241-246.
Mikami, et al. (1987) *FEBS Lett.* 223:273.
Nagy, et al. (1988) *Genes & Develop.* 2:376.
Odell, J. T., Nagy, F., Chua, N. H., (1985) *Nature* 313:810.
Ptashne (1988) *Nature* 335:683.
Sadowski, et al. (1988) *Nature* 335:563.
Sorger and Pelham (1988) *Cell* 54:841.
Strittmatter and Chua (1987) *Pro. Natl. Acad. Sci.* 84:8976.
Velten, et al. (1984) *EMBO J.* 3:2723-30.
Velten and Schell (1985) *Nucleic Acid Res.* 13:6981-98.
Wiederrecht, et al. (1988) *Cell* 54:841.

We claim:

1. A chimeric plant gene which comprises:
   (a) a 5' promoter which functions in plant cells to cause the production of mRNA;
   (b) a structural coding sequence which codes for the production of mRNA encoding the ASF-1 protein; and
   (c) a 3' non-translated region which comprises a polyadenylation signal which causes the addition of polyadenylate nucleotides to the mRNA.

2. A chimeric plant gene of claim 1 in which the promoter is the CaMV35S promoter.

3. A chimeric plant gene of claim 1 in which the promoter is from the small subunit of ribulose bis-phosphate carboxylase gene.

4. A chimeric plant gene of claim 1 in which the promoter is from the chlorophyll A/B binding protein gene.

5. A chimeric plant gene of claim 1 in which the promoter is from a heat-shock protein gene.

6. A chimeric plant gene of claim 1 in which the promoter is from the nopaline synthase gene.

7. A transformed plant cell comprising a gene of claim 1.

8. A transformed plant cell of claim 7 in which the chimeric gene comprises the CaMV35S promoter.

9. A transformed plant cell of claim 7 in which the chimeric gene comprises a promoter from a small subunit of ribulose bis-phosphate carboxylase gene.

10. A transformed plant cell of claim 7 in which the chimeric gene comprises a promoter from a chlorophyll A/B binding protein gene.

11. A transformed plant cell of claim 7 in which the chimeric gene comprises a promoter from a heat-shock protein gene.

12. A transformed plant cell of claim 7 in which the chimeric gene comprises a promoter from a nopaline synthase gene.

* * * * *